(12) United States Patent
Rosa et al.

(10) Patent No.: US 10,028,967 B2
(45) Date of Patent: Jul. 24, 2018

(54) MEDICAMENT

(71) Applicant: Symrise AG, Holzminden (DE)

(72) Inventors: Donna Rosa, Carlstadt, NJ (US); Jakob Ley, Holzminden (DE); Gerhard Krammer, Holzminden (DE); Deborah Kennison, Wayne, NJ (US)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 15/324,457

(22) PCT Filed: Jun. 27, 2015

(86) PCT No.: PCT/EP2015/064627
§ 371 (c)(1),
(2) Date: Jan. 6, 2017

(87) PCT Pub. No.: WO2016/005213
PCT Pub. Date: Jan. 14, 2016

(65) Prior Publication Data
US 2017/0196898 A1     Jul. 13, 2017

Related U.S. Application Data

(60) Provisional application No. 62/022,838, filed on Jul. 10, 2014.

(30) Foreign Application Priority Data

Jul. 30, 2014  (EP) .................................. 14179170

(51) Int. Cl.
| *A61K 31/616* | (2006.01) |
| *A61K 31/485* | (2006.01) |
| *A61K 31/192* | (2006.01) |
| *A61K 31/167* | (2006.01) |
| *A61K 31/137* | (2006.01) |
| *A61K 9/00* | (2006.01) |
| *A61K 47/10* | (2017.01) |
| *A61K 31/09* | (2006.01) |
| *A23L 33/10* | (2016.01) |

(52) U.S. Cl.
CPC ............ *A61K 31/616* (2013.01); *A23L 33/10* (2016.08); *A61K 9/0056* (2013.01); *A61K 9/0095* (2013.01); *A61K 31/09* (2013.01); *A61K 31/137* (2013.01); *A61K 31/167* (2013.01); *A61K 31/192* (2013.01); *A61K 31/485* (2013.01); *A61K 47/10* (2013.01); *A23V 2002/00* (2013.01)

(58) Field of Classification Search
None
See application file for complete search history.

(56) References Cited

U.S. PATENT DOCUMENTS 5,164,398 A * 11/1992 Sims ..................... A61K 31/19
514/282

FOREIGN PATENT DOCUMENTS

| CN | 101 904 850 A | 12/2010 |
| EP | 2 494 953 A1 | 9/2012 |
| WO | 2007/095255 A2 | 8/2007 |
| WO | 2010/100972 A4 | 10/2010 |

* cited by examiner

*Primary Examiner* — Shirley V Gembeh
(74) *Attorney, Agent, or Firm* — Dilworth & Barrese, LLP

(57) ABSTRACT

Suggested is a medicament which is particularly useful for preventing, curing or abating of cough and inflammations of the respiratory system, comprising or consisting of active pharmaceutical ingredients and 1,3-propandiol.

21 Claims, 1 Drawing Sheet

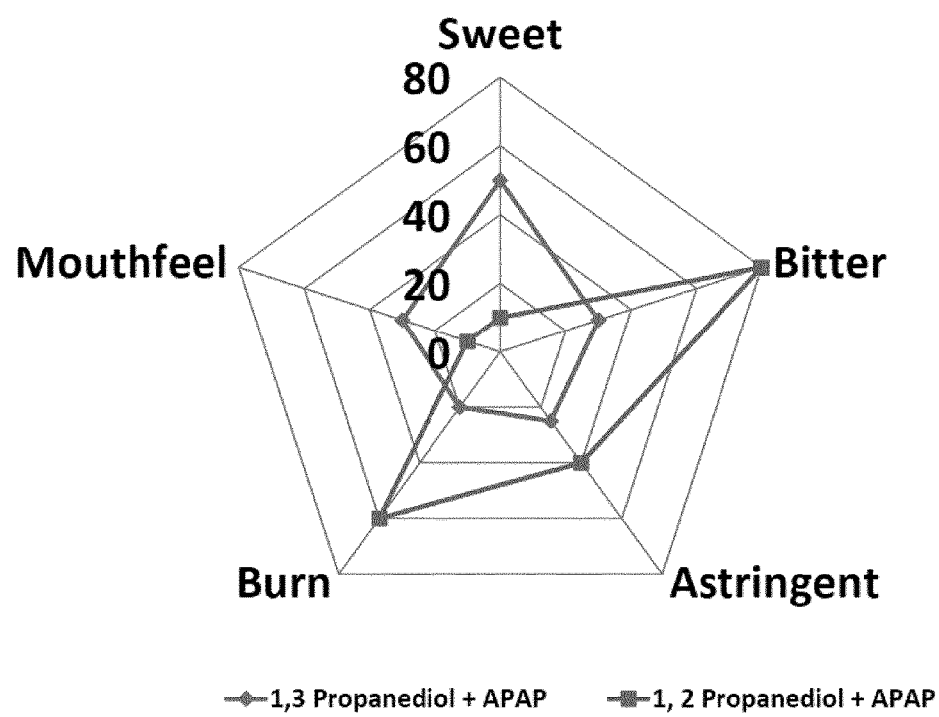
Sensory comparison of APAP active with - 500mg APAP Solution

MEDICAMENT

FIELD OF INVENTION

The present invention belongs to the area of pharmaceuticals and refers to a medicament comprising at least one analgetic and 1,3 propandiol and oral compositions comprising said mixture.

STATE OF THE ART

A cough medicine or a cough and cold medicine, also known as linctus when in syrup form, is a medicinal drug used in those with coughing and related conditions, particularly associated with inflammation of the respiratory system. This could also include liquid medicine for daytime or nightime relief of cold, flu, allergies, or sleeplessness.

Cough medicines typically comprise drugs with painkilling and fever-reducing properties, like for example ibuprofen (IBU) or dextromethorphan (DXM) this is a cough suppressant in quantities of up to 5% b.w. but also actives of natural origin like for example dry extracts of ivy willow is more common for this medical purpose leaves. The medicines are offered in liquid or solid form, as for example syrups, sprays, tablets, pills, capsules, pastilles or hard candies, starch cast strips. Regardless of the galenic presentation, the products suffer from the same disadvantage that is a bitter taste, where traditional solvents often enhance the bitterness caused by the actives.

Most medicinal products have an inherent bitter or unpleasant taste; there is a strong need to overcome this disadvantage in order to improve acceptability of the products, especially when administered to children.

In this context reference is made to U.S. Pat. No. 4,029,797 (FISONS) which discloses a process of utilizing the drug noscapine in a palatable cough syrup which masks the characteristic unpalatable taste of the drug comprising the steps of preparing an alkaline carrier and adding noscapine in a form which is a non-acidic solution, but rather in suspension which is finely dispersed. There is no advice in view of adding a specific taste improver to the active.

British patent application GB 823025A A1 (BASF) discloses polyglycol ether derivative containing 6-12 ethoxy groups prepared from an aliphatic alcohol, carboxylic acid, amine or amide which contains 6-14 carbon atoms by reaction with ethylene oxide or a polyglycol ether of the formula HO(CH2-CH2-O)nH wherein n is 6 to 12. Suitable polyglycol ether derivatives are those of dodecyl, octyl, iso-octyl, nonyl and decyl alcohols, dodecylamine, oleylamine, lauric acid amide, lauryl ethanolamide, dodecylamide, iso-octylamine, lauric and undecylenic acids. The document also discloses a cough remedy comprising said polyglycol ether derivatives in the form of capsules, tablets, pills, intravenous injections, suppositories and a cough syrup. The document is silent with regard of improving taste and acceptance of a medicament containing APIs.

International patent application WO 2007 095255 A2 (DUPONT) refers to a biodegradable composition comprising 1,3-propandiol and active such as for example phenylephrine, ibuprofen or acylsalicylic acid; the amount of 1,3-isopropanol is not disclosed.

International patent application WO 2007 095255 A2 (DUPONT) concerns a pharmaceutical composition comprising factor XI and 5 to 40% b.w. 1,3-propandiol.

European patent application EP 2494953 A1 (NISSAN) discloses a cosmetic composition, comprising ibuprofen or acyl salicylic acid derivatives in combination with 1,3-propandiol as a moisturizer.

Typically, cough medicaments contain propylenglycol (1,2-propandiol) as a solvent, however, propylene glycol often enhances the bitterness of the actives, so that products found in the market typically need to contain high amounts of sweeteners and/or aroma compounds to overcome the bitter taste.

The object of the present invention has been to provide a medicament, in particular a medicament for preventing, curing or abating of cough and inflammation of the respiratory system with improved taste, in particular with reduced bitter taste. Also included are medications for diminishing fever, headache, congestion, sneezing, congestion, and allergy symptoms.

DESCRIPTION OF THE INVENTION

A first object of the present invention relates to a medicament, comprising or consisting of
(a1) at least one active pharmaceutical ingredient according to formula (I)

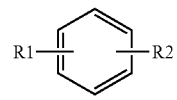

(I)

in which
$R^1$ stands for a hydroxyl, an acyl, a $C_1$-$C_6$ alkyl or a $C_1$-$C_6$ alkoxy radical and
$R^2$ has one of the following meanings:
—$OCOCH_3$;
—$OCH_2CH(OH)CH_2OH$;
—$CH(CH_3)COOH$
—$C(OH)CH_2NHCH_3$;
—NH—COH; or
(a2) dextromethorphan and
(b) 1,3-propandiol,
said 1,3-propandiol being present in an amount of about 1 to about 25% b.w.

A second object of the present invention refers to a medicament comprising or consisting of
(a1) at least one active pharmaceutical ingredient of formula (I) or
(a2) dextromethorphan, and
(b) 1,3-propandiol.
said 1,3-propandiol being present in an amount of about 1 to about 25% b.w. for preventing, curing or abating of cough and inflammations of the respiratory system.

Surprisingly, it has been observed that patients in need of a cough medicine find a medicament comprising an active pharmaceutical ingredient, preferably an analgetic or a soothing agent and 1,3-propandiol as a solvent or diluent having a much better taste, in particular having a significantly reduced bitter-taste compared to a similar product comprising the same amount of 1,2-propandiol.

Active Pharmaceutical Ingredients (API)

Among the active pharmaceutical ingredients, analgetic agents (or used as a synonym: analgesic agents) or soothing agents those are preferred belonging to the group of Nonsteroidal anti-inflammatory drugs, usually abbreviated to NSAIDs also referred to as nonsteroidal anti-inflammatory agents/analgesics (NSAIAs) or nonsteroidal anti-inflammatory medicines (NSAIMs). These compounds represent a class of drugs that provides analgesic (pain-killing) and antipyretic (fever-reducing) effects, and, in higher doses, anti-inflammatory effects. The term nonsteroidal distinguishes these drugs from steroids, which, among a broad range of other effects, have a similar eicosanoid-depressing, anti-inflammatory action. As analgetics, NSAIDs are unusual in that they are non-narcotic and thus are used as a non-addictive alternative to narcotics.

The most prominent members of this group of drugs, aspirin, ibuprofen and naproxen, are all available over the counter in most countries. NSAIDs inhibit the activity of both cyclooxygenase-1 (COX-1) and cyclooxygenase-2 (COX-2), and thereby, the synthesis of prostaglandins and thromboxanes. It is thought that inhibiting COX-2 leads to the anti-inflammatory, analgesic and antipyretic effects and that those NSAIDs also inhibiting COX-1, particularly aspirin, may cause gastrointestinal bleeding and ulcers.

The most preferred API are selected from the group consisting of acetaminophen, phenylephrine, guaifenesin, dextrometorphan, aspirin, ibuprofen, diphenhydramine, various antihistimines, naproxen sodium, and their mixtures. The medicaments according to the invention usually contain at least, often three, four or even all of these compounds. The amounts of the API within a formulation is about 0.1 to about 5% b.w., preferably about 0.5 to about 3% b.w. and particularly about 1 to about 2% b.w.

Acetaminophen

Acetaminophen better know as Paracetamol (abbreviation: APAP) stands for N-acetyl-paminophenol, and is a widely used over-the-counter analgetic (pain reliever) and antipyretic (fever reducer). The product is represented by formula IIa:

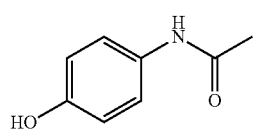

(IIa)

Paracetamol

Paracetamol is classified as a mild analgesic. It is commonly used for the relief of headaches and other minor aches and pains and is a major ingredient in numerous cold and flu remedies. In combination with opioid analgesics, paracetamol can also be used in the management of more severe pain such as post-surgical pain and providing palliative care in advanced cancer patients. Though paracetamol is used to treat inflammatory pain, it is not generally classified as an NSAID because it exhibits only weak anti-inflammatory activity. Paracetamol is the active metabolite of phenacetin and acetanilide, two once popular as an analgesic and antipyretic in its own right. However, unlike phenacetin, acetanilide and their combinations, paracetamol is not considered carcinogenic at therapeutic doses.

Paracetamol is approved for reducing fever in people of all ages and is also used for the relief of pains associated with many parts of the body. It has analgesic properties comparable to those of aspirin, while its anti-inflammatory effects are weaker. It is better tolerated than aspirin in patients in whom excessive gastric acid secretion or prolongation of bleeding time may be a concern. Available without a prescription since 1959,[19] it has since become a common household drug.

Phenylephrine

Phenylephrine is a selective $\alpha_1$-adrenergic receptor agonist used primarily as a decongestant, as an agent to dilate the pupil, and to increase blood pressure. Phenylephrine is marketed as a substitute for the decongestant pseudoephedrine, though clinical studies differ regarding its effectiveness in this role. The compound is represented by formula IIb:

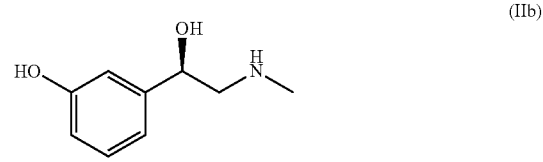

(IIb)

Phenylephrine is used as a decongestant sold as an oral medicine, as a nasal spray, or as eye drops. It is now the most common over-the-counter decongestant in the United States Oral phenylephrine is extensively metabolised by monoamine oxidase, an enzyme that is present in the intestinal wall and in the liver. Compared to intravenous pseudoephedrine, it has a reduced and variable bioavailability; only up to 38%. Because phenylephrine is a selective α-adrenergic receptor agonist, it does not cause the release of endogenous noradrenaline or increase the rate (chronotropy) and strength (inotropy) of heart contractions as pseudoephedrine does.

Phenylephrine is used as a replacement for pseudoephedrine in decongestant medicines due to pseudoephedrine's use in the illicit manufacture of methamphetamine. Its efficacy as an oral decongestant has been questioned, with multiple studies not being able to come to an agreement. Whereas pseudoephedrine causes both vasoconstriction and increase of mucociliary clearance through its nonspecific adrenergic activity, phenylephrine's selective α-adrenergic agonism causes vasoconstriction alone, creating a difference in their methods of action. As a nasal spray, phenylephrine is available in 1% and 0.5% concentrations. It may cause rebound congestion, similar to oxymetazoline.

Guaifenesin

Guaifenesin or guaiphenesin also known as glyceryl guaiacolate, is an expectorant drug sold over the counter and usually taken orally to assist the bringing up (expectoration) of phlegm from the airways in acute respiratory tract infections. The compound is represented by formula IIc:

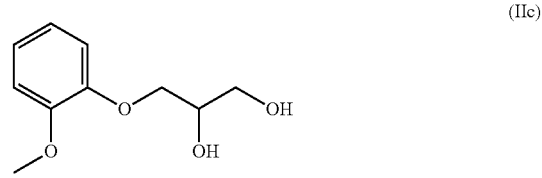

(IIc)

Similar medicines derived from the guaiac tree were in use as a generic remedy by American indigenous peoples when explorers reached North America in the 16th century. The Spanish encountered guaiacum wood "when they conquered Santo Domingo; it was soon brought back to Europe, where it acquired an immense reputation in the sixteenth century as a cure for syphilis and certain other diseases. The 1955 edition of the *Textbook of Pharmacognosy* states: "Guaiacum has a local stimulant action which is sometimes useful in sore throat. The resin is used in chronic gout and rheumatism, whilst the wood is an ingredient in the compound concentrated solution of sarsaparilla, which was formerly much used as an alternative in syphilis.

The principal use of guaifenesin is in the treatment of coughing. A Cochrane Collaboration meta-analysis of over-the-counter medicines for acute cough in children and adults concluded that there was not enough high-quality clinical data to prove or disprove the effectiveness of any examined drug including guaifenesin.[6] Guaifenesin is sometimes combined with dextromethorphan, an antitussive, such as in Mucinex DM or Robitussin DM.

Guaifenesin is thought to act as an expectorant by increasing the volume and reducing the viscosity of secretions in the trachea and bronchi. It also stimulates the flow of respiratory tract secretions, allowing ciliary movement to carry the loosened secretions upward toward the pharynx. Thus, it may increase the efficiency of the cough reflex and facilitate removal of the secretion.

Dextromethorphan

Dextromethorphan (DXM or DM) is an antitussive (cough suppressant) drug. It is one of the active ingredients in many over-the-counter cold and cough medicines, including generic labels and store brands, Benylin DM, Mucinex DM, Robitussin, NyQuil, Dimetapp, Vicks, Coricidin, Delsym, TheraFlu, and others. Dextromethorphan has also found other uses in medicine, ranging from pain relief to psychological applications. It is sold in syrup, tablet, spray, and lozenge forms. In its pure form, dextromethorphan occurs as a white powder. The compound is represented by formula IId:

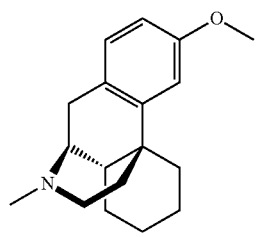

(IId)

The primary use of dextromethorphan is as a cough suppressant, for the temporary relief of cough caused by minor throat and bronchial irritation (such as commonly accompanies the flu and common cold), as well as those resulting from inhaled particle irritants. A combination of dextromethorphan and quinidine, a CYP2D6 inhibitor, has been shown to alleviate symptoms of easy laughing and crying (pseudobulbar affect) in patients with amyotrophic lateral sclerosis and multiple sclerosis.

Aspirin

Aspirin, also known as acetylsalicylic acid, is a salicylate drug, often used as an analgesic to relieve minor aches and pains, as an antipyretic to reduce fever, and as an anti-inflammatory medication. The compound is represented by formula IIe:

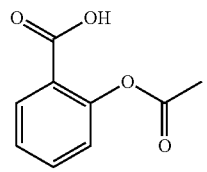

(IIe)

Aspirin also has an antiplatelet effect by inhibiting the production of thromboxane, which under normal circumstances binds platelet molecules together to create a patch over damaged walls of blood vessels. Because the platelet patch can become too large and also block blood flow, locally and downstream, aspirin is also used long-term, at low doses, to help prevent heart attacks, strokes, and blood clot formation in people at high risk of developing blood clots. It has also been established that low doses of aspirin may be given immediately after a heart attack to reduce the risk of another heart attack or of the death of cardiac tissue. Aspirin may be effective at preventing certain types of cancer, particularly colorectal cancer.

Aspirin is part of a group of medications called nonsteroidal anti-inflammatory drugs (NSAIDs), but differs from most other NSAIDs in the mechanism of action. Though it, and others with similar structure called the salicylates, have similar effects (antipyretic, anti-inflammatory, analgesic) to the other NSAIDs and inhibit the same enzyme cyclooxygenase (COX), aspirin (but not the other salicylates) does so in an irreversible manner and, unlike others, affects more the COX-1 variant than the COX-2 variant of the enzyme.

Aspirin is generally considered inferior to ibuprofen for the alleviation of pain because aspirin is more likely to cause gastrointestinal bleeding. Aspirin is generally ineffective for those pains caused by muscle cramps, bloating, gastric distension, or acute skin irritation.[23] As with other NSAIDs, combinations of aspirin and caffeine provide slightly greater pain relief than aspirin alone. Effervescent formulations of aspirin, such as Alka-Seltzer or Blowfish, relieve pain faster than aspirin in tablets, which makes them useful for the treatment of migraines. Topical aspirin may be effective for treating some types of neuropathic pain Like its ability to control pain, aspirin's ability to control fever is due to its action on the prostaglandin system through its irreversible inhibition of COX.

Ibuprofen

Ibuprofen stands for isobutylphenylpropanoic acid and represents a nonsteroidal anti-inflammatory drug (NSAID) used for relieving pain, helping with fever, and reducing inflammation. The compound is represented by formula IIf:

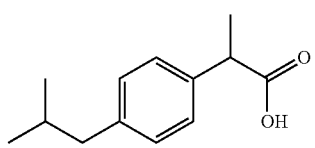

(IIf)

Ibuprofen has an antiplatelet effect, though it is relatively mild and somewhat short-lived compared with aspirin or prescription antiplatelet drugs. In general, ibuprofen also has a vasodilation effect.

Ibuprofen was derived from propanoic acid by the research arm of Boots Company during the 1960s and patented in 1961. Originally marketed as Brufen, ibuprofen is available under a variety of popular trademarks, including Motrin, Nurofen, Advil, Nuprin and many others. Generic formulations are available as well. It is on the World Health Organization's List of Essential Medicines, a list of the most important medication needed in a basic health system. Ibuprofen is used primarily for fever, pain, painful periods and inflammatory diseases such as osteoarthritis and rheumatoid arthritis. It is also used for pericarditis and patent ductus arteriosus.

1,3-Propandiol 1,3-Propandiol is a well-known solvent that is chemically synthesised by hydrogenation of acrolein, or by hydroformylation of ethylene glycol to afford 3-hydroxy propionaldehyde, which is subsequently hydrogenated to give 1,3-propandiol.

1,3-propanediol is commercially sold as ZEMEA@ from DuPont Tate & Lyle BioProducts (Wilmington; DE). Other sources of 1,3-propanediol including products from natural sources may be used as well.

The preferred amounts of 1,3-propandiol in the medicaments is about 2 to about 15% b.w. and particularly about 5 to about 10% b.w.

1,3-propandiol can be added to the API as a solvent or diluent forming a binary composition or can be introduced into the medicament as a part of a flavour composition that is blended with the API.

FIG. 1 provides a sensory comparison indicating that 1,3-propandiol shows an improved sensory profile compared to 1,2-propandiol.

Aroma Compounds

According to another preferred embodiment of the present invention the medicament may contain at least one aroma compound, preferably at least one traditional flavour or a flavour modulating compound.

The compounds can be chosen from synthetic flavouring liquid and/or oils derived from plants leaves, flowers, fruits and so forth, and combinations thereof. Representative flavouring liquids include: artificial, natural or synthetic fruit flavours such as *eucalyptus*, lemon, orange, banana, grape, lime, apricot and grapefruit oils and fruit essences including apple, strawberry, cherry, orange, pineapple and so forth; bean and nut derived flavours such as coffee, cocoa, cola, peanut, almond and so forth; and root derived flavours such as licorice or ginger.

The flavouring agent is preferably selected from the group consisting of essential oils and extracts, tinctures and balsams, such as, for example, anisole, basil oil, bergamot oil, bitter almond oil, camphor oil, citronella oil, lemon oil; *Eucalyptus citriodora* oil, *eucalyptus* oil, fennel oil, grapefruit oil, camomile oil, spearmint oil, caraway oil, lime oil, mandarin oil, nutmeg oil (in particular nutmeg blossom oil=maces oil, mace oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if the flavoured composition according to the invention comprises at least one flavouring agent, preferably two, three, four, five, six, seven, eight or more flavouring agents chosen from the following group: menthol (preferably I-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, limonene (preferably D-limonene, optionally as a constituent of an essential oil), piperitone, transsabinene hydrate, menthofuran, caryophyllene, germacrene D, cinnamaldehyde, mint lactone, thymol, gamma-octalactone, gamma-nonalactone, gamma-decalactone, (1,3E,5Z)undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

In particular preferred aroma or flavouring compounds encompass menthol, cineol, eugenol, thymol, cinnamic aldehyde, peppermint oil, spearmint oil, *eucalyptus* oil, thyme oil, cinnamon oil, clove oil, spruce needle oil, fennel oil, sage oil, aniseed oil, star anise oil, chamomile oil, and caraway oil, and their mixtures. In the US fruit flavors (especially cherry, grape, citrus and berry) are preferred in these preparations, especially for pediatric products.

The most preferred flavour modulating compounds are selected from the group consisting of vanillin, pellitorine, homoeriodictyol, eriodictyol, hesperetin, and phloretin.

The aroma compounds can be present in amounts of about 0.1 to about 5% b.w., preferably about 0.5 to about 3% b.w. and in particular about 1 to about 2% b.w.

Galenic Forms

In a first preferred embodiment of the invention the medicament is in liquid form, wherein said liquid could be for example a cough syrup, drinkable liquid, or a cough spray.

In a second preferred embodiment of the invention the medicament is in solid form, wherein said solid could be a tablet, a capsule, a pill, a pastille or a (hard boiled) candy. Include liquid and solid filled capsules.

The veracious galenic forms may include other additives which are exemplified further below.

Oral Compositions

Finally, another object of the present invention is directed to a preferably nontherapeutic oral composition comprising or consisting of (a1) at least one active pharmaceutical ingredient of formula (I) or (a2) dextromethorphan, and (b) 1,3-propandiol said 1,3-propandiol being present in an amount of about 1 to about 25% b.w.

Typical examples for suitable oral compositions encompass (hard boiled) candies, compressed tablets, chewing gums, toothpastes and mouth washes. The manufacture and composition of said oral compositions are described as follows:

Candies

According to the present invention the preferred candies are so-called hard-boiled candies. Their bases are usually prepared from a mixture of sugar and other carbohydrates that are kept in an amorphous or glassy condition. This form can be considered a solid syrup of sugars generally having up to about 4.5% b.w. moisture, based on the weight of the candy base, with about 0.5 to about 2.5% b.w. being preferred and about 1.0 to about 1.5% b.w. being most preferred. Such materials normally contain up to 65% b.w. corn syrup, up to 80% b.w. sugar and from 0.1 to 5.0% b.w. water. Generally, the ratio of sugar (or other sweetener suitable for candy formulation) to corn syrup is within the range of about 70:25 to about 45:55 with about 60:40 being preferred. The syrup component generally is prepared from corn syrups high in fructose, but may include other materials. Further ingredients such as flavourings, sweeteners, acidulents, colorants and so forth may also be added.

Hard boiled candy bases may also be prepared from non-fermentable sugars such as sorbitol, mannitol, xylitol, maltitol, hydrogenated starch hydrolysate, hydrogenated corn syrup and mixtures thereof. The candy bases may contain up to about 95% sorbitol, a mixture of sorbitol and mannitol at a ratio of about 9.5% to 0.5% up to about 7.5% to 2.5% and hydrogenated corn syrup up to about 55% of the syrup component.

Compressed Tablets

According to the present invention the oral compositions can represent compressed tablets, comprising the liquid flavour in amounts of typically about 0.1 to about 0.6% b.w. and preferably about 0.5% b.w. The amount of hydroxy alpha-sanshool and/or 2-phenyl butenal in amounts of from about 0.01 to about 0.07% b.w. and preferably about 0.05% b.w.

Chewing Gums

Chewing gums typically consist of a water-insoluble phase component, a water-soluble component and additives providing for example a specific flavour.

The water-insoluble base, which is also known as the "gum base", typically comprises natural or synthetic elastomers, resins, fats and oils, plasticizers, fillers, softeners, dyes and optionally waxes. The base normally makes up 5 to 95% by weight, preferably 10 to 50% by weight and more particularly 20 to 35% by weight of the composition as a whole. In one typical embodiment of the invention, the base consists of 20 to 60% by weight synthetic elastomers, 0 to 30% by weight natural elastomers, 5 to 55% by weight plasticizers, 4 to 35% by weight fillers, 5 to 35% by weight softeners and small amounts of additives, such as dyes, antioxidants and the like, with the proviso that they are soluble in water at best in small quantities.

Suitable synthetic elastomers are, for example, polyisobutylenes with average molecular weights (as measured by GPC) of 10,000 to 100,000 and preferably 50,000 to 80,000, isobutylene/isoprene copolymers ("butyl elastomers"), styrene/butadiene copolymers (styrene:butadiene ratio, for example, 1:3 to 3:1). polyvinyl acetates with average molecular weights (as measured by GPC) of 2,000 to 90,000 and preferably 10,000 to 65,000, polyisoprenes, poly-ethylenes, vinyl acetate/vinyl laurate copolymers and mixtures thereof. Examples of suitable natural elastomers are rubbers, such as for example smoked or liquid latex or guayuls, and natural gums, such as jelutong, lechi caspi, perillo, sorva, massaranduba balata, massaranduba chocolate, nispero, rosindinba, chicle, gutta hang kang and mixtures thereof. The choice of the synthetic and natural elastomers and their mixing ratios essentially depends on whether or not bubbles are to be produced with the chewing gums (bubble gums). Elastomer mixtures containing jelutong, chicle, sorva and massaranduba are preferably used.

In most cases, the elastomers are too hard or lack plasticity for satisfactory processing, so that it has been found to be of advantage to use special plasticizers which, of course, must also satisfy in particular all requirements relating to acceptability as food additives. In this respect, suitable plasticizers are, above all, esters of resin acids, for example esters of lower aliphatic alcohols or polyols with completely or partly hydrogenated, monomeric or oligomeric resin acids. In particular, the methyl, glycerol or pentaerythritol esters or mixtures thereof are used for this purpose. Alternatively, terpene resins, which may be derived from .alpha.-pinene, .beta.-pinene, .delta.-limonene or mixtures thereof, could also be used.

Suitable fillers or texturizers are magnesium or calcium carbonate, ground pumice stone, silicates, especially magnesium or aluminium silicates, clays, aluminium oxides, talcum, titanium dioxide, mono-, di- and tricalcium phosphate and cellulose polymers.

Suitable softeners or emulsifiers are tallow, hydrogenated tallow, hydrogenated or partly hydrogenated vegetable oils, cocoa butter, partial glycerides, lecithin, triacetin and saturated or unsaturated fatty acids containing 6 to 22 and preferably 12 to 18 carbon atoms and mixtures thereof.

Suitable dyes and whiteners are, for example, the FD&C types, plant and fruit extracts permitted for colouring foods and titanium dioxide. The gum bases may also contain waxes or may be wax-free In addition to the water-insoluble gum base, chewing gum preparations regularly contain a water-soluble component which is formed, for example, by softeners, sweeteners, fillers, flavours, flavour enhancers, emulsifiers, dyes, acidifiers, antioxidants and the like, with the proviso that the constituents have at least adequate solubility in water. Accordingly, individual constituents may belong both to the water-insoluble phase and to the water-soluble phase, depending on the water solubility of the special representatives. However, combinations may also be used, for example a combination of a water-soluble and a water-insoluble emulsifier, in which case the individual representatives are present in different phases. The water-insoluble component usually makes up 5 to 95% by weight and preferably 20 to 80% by weight of the preparation.

Water-soluble softeners or plasticizers are added to the chewing gum compositions to improve chewability and the chewing feel and are present in the mixtures in quantities of typically 0.5 to 15% by weight. Typical examples are glycerol, lecithin and aqueous solutions of sorbitol, hydrogenated starch hydrolysates or corn syrup.

Fillers are particularly suitable for the production of low-calorie chewing gums and may be selected, for example, from polydextrose, raftilose, raftilin, fructo-oligosaccharides (NutraFlora), palatinose oligosaccharides, guar gum hydrolyzates (Sun Fiber) and dextrins.

The chewing gums may additionally contain auxiliaries and additives which are suitable, for example, for dental care, more particularly for controlling plaque and gingivitis, such as for example chlorhexidine, CPC or triclosan. They may also contain pH adjusters (for example buffer or urea), anti-caries agents (for example phosphates or fluorides), biogenic agents (antibodies, enzymes, caffeine, plant extracts), providing these substances are permitted in foods and do not undesirably interact with one another.

Toothpastes and Mouth Washes

Toothpastes or tooth creams are generally understood to be paste-like preparations of water, thickeners, humectants, abrasives or polishes, surfactants, sweeteners, flavorings, deodorizing agents and agents active against oral and dental diseases. In toothpastes according to the invention, any of the usual polishes may be used, such as chalk, dicalcium phosphate, insoluble sodium metaphosphate, aluminium silicates, calcium pyrophosphate, finely particulate synthetic resins, silicas, aluminium oxide and aluminium oxide trihydrate. Particularly suitable polishes for toothpastes according to the invention are finely particulate xerogel silicas, hydrogel silicas, precipitated silicas, aluminium oxide trihydrate and finely particulate .alpha.-alumina, or mixtures of these polishes. Such polishes are preferably used in quantities of from about 15 to 40% by weight of the toothpaste. Preferred humectants used for toothpastes according to the invention include low molecular weight polyethylene glycols, glycerol, sorbitol or mixtures thereof in quantities of up to about 50% by weight of the toothpaste. Among the known thickeners for use with toothpastes according to the invention, particularly preferred are the thickening, finely particulate gel silicas and nonionic hydrocolloids, such as hydroxy ethyl cellulose, hydroxy propyl guar, hydroxy ethyl starch, polyvinyl pyrrolidone, high molecular weight polyethylene glycol and vegetable gums, such as tragacanth, agaragar, carrageen moss, gum arabic and xanthan gum. The desired flavor and aroma for preparations in accordance with the invention may be obtained by adding the components (a) and/or (b) and optionally also (c). It is also advantageous adding caries inhibitors to the oral preparations in the form of, for example, alkali fluorides, alkali monofluorophosphates or alkali salts of organophosphonic acids. In addition, the oral preparations according to the invention may contain other standard auxiliaries, such as dyes, preservatives and opacifiers, for example titanium dioxide. For mouthwashes, the oral compositions according to the invention may readily be combined with aqueous-alcoholic solutions containing different amounts of ethereal oils, emulsifiers, astringent and toning drug extracts, caries-inhibiting additives and flavour correctants.

Additives

The oral compositions of the present invention may include additional additives as for examples sweeteners or vitamins, in amounts of from about 0.1 to about 10% b.w. These additives may also represent components of the respective medicaments.

Sweeteners

Suitable sweet-tasting substances, including natural sources of these substances (component e5), such as for example sweet-tasting carbohydrates or sugars (e.g. sucrose (synonymous with saccharose), trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrin) or vegetable preparations containing predominantly these carbohydrates (e.g. from sugar beet (*Beta vulgaris* ssp., sugar fractions, sugar syrup, molasses), from sugar cane (*Saccharum officinarum* ssp., e.g. molasses, sugar syrups), from sugar maple (*Acer* ssp.), from agave (agave thick juice), synthetic/enzymatic hydrolysates of starch or sucrose (e.g. invert sugar syrup, highly enriched fructose syrups made from corn starch), fruit concentrates (e.g. from apples or pears, apple syrup, pear syrup), sugar alcohols (e.g. erythritol, threitol, arabitol, ribitol, xylitol, sorbitol, mannitol, dulcitol, lactitol), proteins (e.g. miraculin, monellin, thaumatin, curculin, brazzein), sweeteners (magap, sodiumcyclamate, acesulfame K, neohesperidin dihydrochalcone, saccharin sodium salt, Aspartame®, superaspartame, neotame, alitame, sucralose, stevioside, rebaudioside, lugduname, carrelame, sucrononate, sucrooctate, monatin, phyllodulcin), certain sweet-tasting amino acids (glycine, D-leucine, D-threonine, D-asparagine, D-phenylalanine, D-tryptophan, L-proline), other sweet-tasting low-molecular substances (e.g. hernandulcin, phyllodulcin, dihydrochalcone glycosides, glycyrrhizin, glycyrrhetinic acid ammonium salt or other glycyrrhetinic acid derivatives), liquorice extracts (*Glycyrrhizza glabra* ssp.), *Lippia dulcis* extracts, *Momordica* ssp. extracts or individual substances (in particular *Momordica grosvenori* [Luo Han Guo] and the mogrosides obtained therefrom), *Hydrangea dulcis* or *Rubus suavissimis* or *Stevia* ssp. (e.g. *Stevia rebaudiana*) extracts or individual substances or derivatives produced by fermentative or enzymatic conversion.

Vitamins

In another embodiment of the present invention the compositions may include vitamins (component e1). Vitamins have diverse biochemical functions. Some have hormone-like functions as regulators of mineral metabolism (e.g., vitamin D), or regulators of cell and tissue growth and differentiation (e.g., some forms of vitamin A). Others function as antioxidants (e.g., vitamin E and sometimes vitamin C). The largest numbers of vitamins (e.g. B complex vitamins) act as precursors for enzyme cofactors that help enzymes in their work as catalysts in metabolism. In this role, vitamins may be tightly bound to enzymes as part of prosthetic groups: For example, biotin is part of enzymes involved in making fatty acids. Vitamins may also be less tightly bound to enzyme catalysts as coenzymes, detachable molecules that function to carry chemical groups or electrons between molecules. For example, folic acid carries various forms of carbon group—methyl, formyl, and methylene—in the cell. Although these roles in assisting enzyme-substrate reactions are vitamins' best-known function, the other vitamin functions are equally important. In the course of the present invention suitable vitamins are selected from the group consisting of Vitamin A (retinol, retinal, beta carotene),
Vitamin $B_1$ (thiamine),
Vitamin $B_2$ (riboflavin),
Vitamin $B_3$ (niacin, niacinamide),
Vitamin $B_5$ (panthothenic acid),
Vitamin $B_6$ (pyridoxine, pyridoxamine, paridoxal),
Vitamin $B_7$ (biotin),
Vitamin $B_9$ (folic acid, folinic acid),
Vitamin $B_{12}$ (cyanobalamin, hydoxycobalmin, methylcobalmin),
Vitamin C (ascorbic acid),
Vitamin D (cholecalciferol),
Vitamin E (tocopherols, tocotrienols), and
Vitamin K (phyolloquinone, menaquinone).

The preferred vitamins are ascorbic acid and tocopherols.

Examples

Formulations Examples for Oral Compositions

The following Tables B1 to B5 provide various examples for oral compositions

TABLE B1

| Chewing gum. free of sugar; all amounts in % b.w. | | | |
|---|---|---|---|
| Composition | B1-1 | B1-2 | B1-3 |
| Gum base | 30.00 | 30.00 | 30.00 |
| Sorbit, powdered | 40.00 | 40.00 | 40.00 |
| Acetaminophen | 0.2 | — | 0.2 |
| Phenylephrine | — | 0.2 | 0.2 |
| Guaifenesin | 0.3 | 0.3 | 0.3 |
| Dextrometorphan | 0.4 | 0.4 | 0.4 |
| Acetyl salicylic acid | 0.2 | 0.2 | 0.2 |
| Ibuprofen | 0.4 | 0.4 | 0.4 |
| Isomalt, powdered | 9.50 | 9.50 | 9.50 |
| Xylitol | 2.00 | 2.00 | 2.00 |
| Mannit D | 3.00 | 3.00 | 3.00 |
| Aspartame | 0.10 | 0.10 | 0.10 |
| Acesulfam K | 0.10 | 0.10 | 0.10 |
| Emulgum/ Plasticizing agent | 0.30 | 0.30 | 0.30 |
| 1,3-Propandiol | 2.00 | 2.00 | 2.00 |
| Sorbitol (70% water) | | Add 100 | |

TABLE B2

Tooth paste; all amounts in % b.w.

| Composition | B2-1 | B2-2 | B2-3 |
|---|---|---|---|
| Dicalciumphosphate dihydrate | 36.00 | 36.00 | 36.00 |
| Acetaminophen | 0.2 | — | 0.2 |
| Phenylephrine | — | 0.2 | 0.2 |
| Guaifenesin | 0.3 | 0.3 | 0.3 |
| Dextrometorphan | 0.4 | 0.4 | 0.4 |
| Acetyl salicylic acid | 0.2 | 0.2 | 0.2 |
| Ibuprofen | 0.4 | 0.4 | 0.4 |
| Solbrol M (sodium salt) | 0.15 | 0.15 | 0.15 |
| Sodium monofluor phosphate | 0.76 | 0.76 | 0.76 |
| Saccharin | 0.20 | 0.20 | 0.20 |
| Aerosil 200 | 3.00 | 3.00 | 3.00 |
| Sodium carboxymethyl cellulose | 1.20 | 1.20 | 1.20 |
| Sodium lauryl sulfate | 1.30 | 1.30 | 1.30 |
| 1,3-Propandiol | 4.0 | 4.0 | 4.0 |
| Glycerol | 16.0 | 16.0 | 16.0 |
| Deionised water | | Ad 100 | |

TABLE B3

Mouth wash concentrate; all amounts in % b.w.

| Composition | B3-1 | B3-2 | B3-3 |
|---|---|---|---|
| Ethanol 96% | 38.00 | 38.00 | 38.00 |
| Cremophor RH 455 | 5.00 | 5.00 | 5.00 |
| Acetaminophen | 0.2 | — | 0.2 |
| Phenylephrine | — | 0.2 | 0.2 |
| Guaifenesin | 0.3 | 0.3 | 0.3 |
| Dextrometorphan | 0.4 | 0.4 | 0.4 |
| Acetyl salicylic acid | 0.2 | 0.2 | 0.2 |
| Ibuprofen | 0.4 | 0.4 | 0.4 |
| Allantoin | 0.20 | 0.20 | 0.20 |
| Sodium saccharin 450 | 0.10 | 0.10 | 0.10 |
| Colour L-Blue 5000 (1% in Wasser) | 0.03 | 0.03 | 0.03 |
| 1,3-Propandiol | 4.0 | 4.0 | 4.0 |
| Peppermint aroma | — | 2.00 | — |
| Deionised water | | Ad 100 | |

TABLE B4

Hard boiled candy, sugar-free; all amounts in % b.w.

| Composition | B4-1 | B4-2 | B4-3 |
|---|---|---|---|
| Xylitol | 2.40 | 2.40 | 2.40 |
| Acetaminophen | 0.2 | — | 0.2 |
| Phenylephrine | — | 0.2 | 0.2 |
| Guaifenesin | 0.3 | 0.3 | 0.3 |
| Dextrometorphan | 0.4 | 0.4 | 0.4 |
| Acetyl salicylic acid | 0.2 | 0.2 | 0.2 |
| Ibuprofen | 0.4 | 0.4 | 0.4 |
| 1,3-Propandiol | 0.2 | 0.2 | 0.2 |
| Sucralose | 0.03 | 0.03 | 0.03 |
| Acesulfame K | 0.050 | 0.050 | 0.050 |
| Citric acid | 0.050 | 0.050 | 0.050 |
| Water | 2.24 | 2.24 | 2.24 |
| Isomalt | | Ad 100 | |

TABLE B5

Hard boiled candy; all amounts in % b.w.

| Composition | B5-1 | B5-2 | B5-3 |
|---|---|---|---|
| Water | 2.75 | 2.24 | 2.24 |
| Acetaminophen | 0.2 | — | 0.2 |
| Phenylephrine | — | 0.2 | 0.2 |
| Guaifenesin | 0.3 | 0.3 | 0.3 |
| Dextrometorphan | 0.4 | 0.4 | 0.4 |
| Acetyl salicylic acid | 0.2 | 0.2 | 0.2 |
| Ibuprofen | 0.4 | 0.4 | 0.4 |
| 1,3-Propandiol | 4.0 | 4.0 | 4.0 |
| Glucose syrup | 32.9 | 32.40 | 32.40 |
| Glucose | | Ad 100 | |

The invention claimed is:

1. A An orally ingestible medicament, comprising
   (a) at least one active pharmaceutical ingredient selected from the group consisting of acetaminophen, phenylephrine, guaifenesin, dextromethorphan, aspirin, ibuprofen and their mixtures

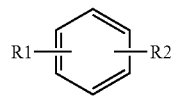

and
   (b) 1,3-propandiol,
   said 1,3-propandiol being present in an amount of about 2 to about 25 b.w., for the treatment of cough and inflammations of the respiratory system, the medicament formulated for oral ingestion.

2. The medicament of claim 1 containing about 2 to about 15% b.w. 1,3-propandiol.

3. The medicament of claim 1, further comprising at least one aroma compound.

4. The medicament of claim 3, wherein said aroma compound is a flavour modulating compound.

5. The medicament of claim 4, wherein said flavour modulating compound is selected from the group consisting of vanillin, pellitorine and HED.

6. The medicament of claim 1 being in liquid form.

7. The medicament of claim 6, wherein said liquid is in the form of a cough syrup or a cough spray.

8. The medicament of claim 7, wherein the medicament comprises dextromethorphan or guaifenesin.

9. The medicament of claim 1 being in solid form.

10. A The medicament of claim 9, wherein said solid is tablet, a capsule, a pill, a pastille or a hard candy.

11. A method for treating cough and inflammation of the respiratory system, comprising orally administering a pharmaceutically effective amount of the medicament of claim 1 to a patient in need thereof.

12. The method of claim 11, wherein the medicament comprises dextromethorphan or guaifenesin.

13. A medicament, comprising
   (a) dextromethorphan, and
   (b) 1,3-propandiol,
said 1,3-propandiol being present in an amount of about 2 to about 25% b.w., for the treatment of cough and inflammations of the respiratory system, the medicament formulated for oral ingestion.

14. The medicament of claim 13, further comprising, guaifenesin.

15. The medicament of claim 13 containing about 2 to about 15% b.w. 1,3-propandiol.

16. The medicament of claim 13, further comprising at least one aroma compound.

17. The medicament of claim 13 being in liquid form.

18. The medicament of claim 13 being in solid form.

19. A method for treating cough and inflammation of the respiratory system, comprising orally administering a pharmaceutically effective amount of the medicament of claim 13 to a patient in need thereof.

20. An oral composition in liquid or solid form, comprising
    (a1) at least one active pharmaceutical ingredient according to formula (I)

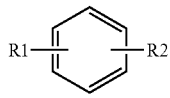
(I)

in which
    $R^1$ is a hydroxyl, an acyl, a $C_1$-$C_6$ alkyl or a $C_1$-$C_6$ alkoxy radical, and
    $R^2$ is one of the following:
        —$OCOCH_3$;
        —$OCH_2CH(OH)CH_2OH$;
        —$CH(CH_3)COOH$;
        —$C(OH)CH_2NHCH_3$;
        —NH—COH; or
    (a2) dextomethorphan, and
    (b) 1,3-propandiol
    said 1,3-propandiol being present in an amount of about 2 to about 25% b.w. and said medicament formulated for oral ingestion.

21. The composition of claim 20, pharmaceutically formulated in the form of a cough syrup, a cough spray, a tablet, a capsule, a pill, a pastille or a hard candy.

* * * * *